(12) United States Patent
Rovner

(10) Patent No.: US 8,608,782 B1
(45) Date of Patent: Dec. 17, 2013

(54) SCOLIOSIS DE-ROTATION SYSTEM AND METHOD

(76) Inventor: Robert A. Rovner, Danville, CA (US)

( * ) Notice: Subject to any disclaimer, the term of this patent is extended or adjusted under 35 U.S.C. 154(b) by 0 days.

(21) Appl. No.: 12/931,824

(22) Filed: Feb. 10, 2011

(51) Int. Cl.
A61B 17/70 (2006.01)
(52) U.S. Cl.
USPC ........... 606/264; 606/265; 606/86 A; 606/914
(58) Field of Classification Search
USPC .................................... 606/59, 264–275, 103
See application file for complete search history.

(56) References Cited

U.S. PATENT DOCUMENTS

| 3,865,105 | A  | * | 2/1975 | Lode ............................... 606/54 |
| 4,078,559 | A  | * | 3/1978 | Nissinen ........................ 606/258 |
| 6,371,957 | B1 | * | 4/2002 | Amrein et al. ................. 606/272 |
| 6,755,828 | B2 | * | 6/2004 | Shevtsov et al. ................ 606/54 |
| 7,678,137 | B2 | * | 3/2010 | Butler et al. ................... 606/246 |
| 2005/0033291 | A1 | * | 2/2005 | Ebara ............................. 606/53 |
| 2006/0149236 | A1 | * | 7/2006 | Barry .............................. 606/61 |
| 2006/0271050 | A1 | * | 11/2006 | Piza Vallespir ................. 606/61 |
| 2007/0213716 | A1 | * | 9/2007 | Lenke et al. .................... 606/61 |
| 2009/0204159 | A1 | * | 8/2009 | Justis et al. .................... 606/323 |
| 2011/0172714 | A1 | * | 7/2011 | Boachie-Adjei et al. ..... 606/264 |
| 2012/0035668 | A1 | * | 2/2012 | Manninen et al. ............ 606/305 |

* cited by examiner

Primary Examiner — Eduardo C Robert
Assistant Examiner — Jerry Cumberledge
(74) Attorney, Agent, or Firm — Heisler & Associates

(57) ABSTRACT

The system includes multiple pedicle screws anchored to multiple vertebra, at least one of which needs to be de-rotated about a central spine axis relative to adjacent vertebrae. Elongate posts are attached to the pedicle screws and extend away from the pedicle screws. A holder, such as in the form of multiple clamps and bars and a de-rotation rod, hold the posts together after de-rotation of a mis-rotated vertebra. With the vertebra held where desired, a spine rod can then be attached to heads of the pedicle screws to hold the vertebrae in their desired positions. After spine rod attachment, the posts and associated portions of the system other than the pedicle screws and spine rods can then be removed, with the pedicle screws and spine rods typically remaining implanted to hold the vertebrae in their desired and de-rotated positions.

2 Claims, 5 Drawing Sheets

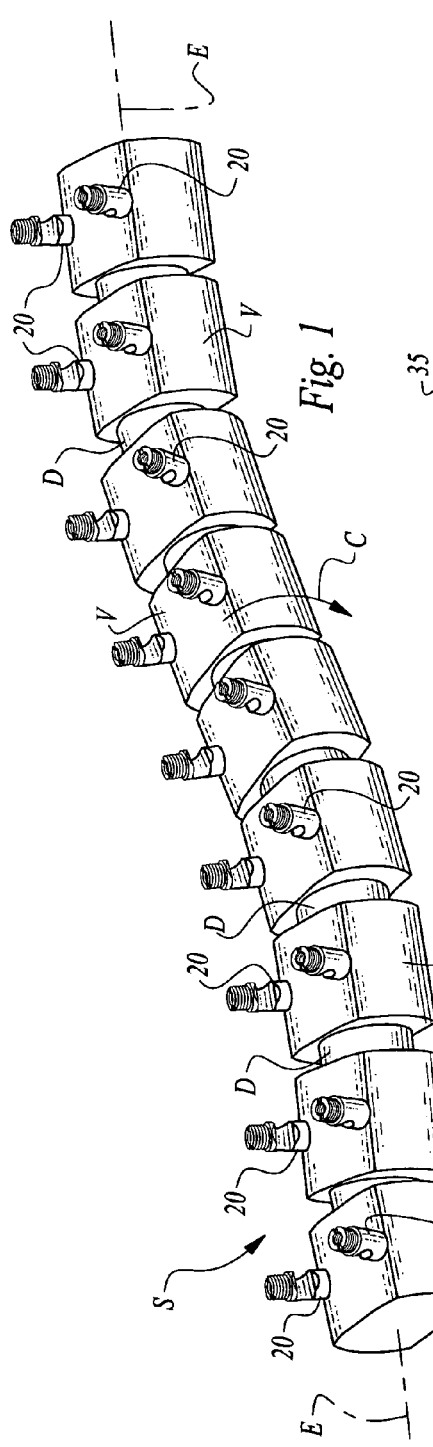
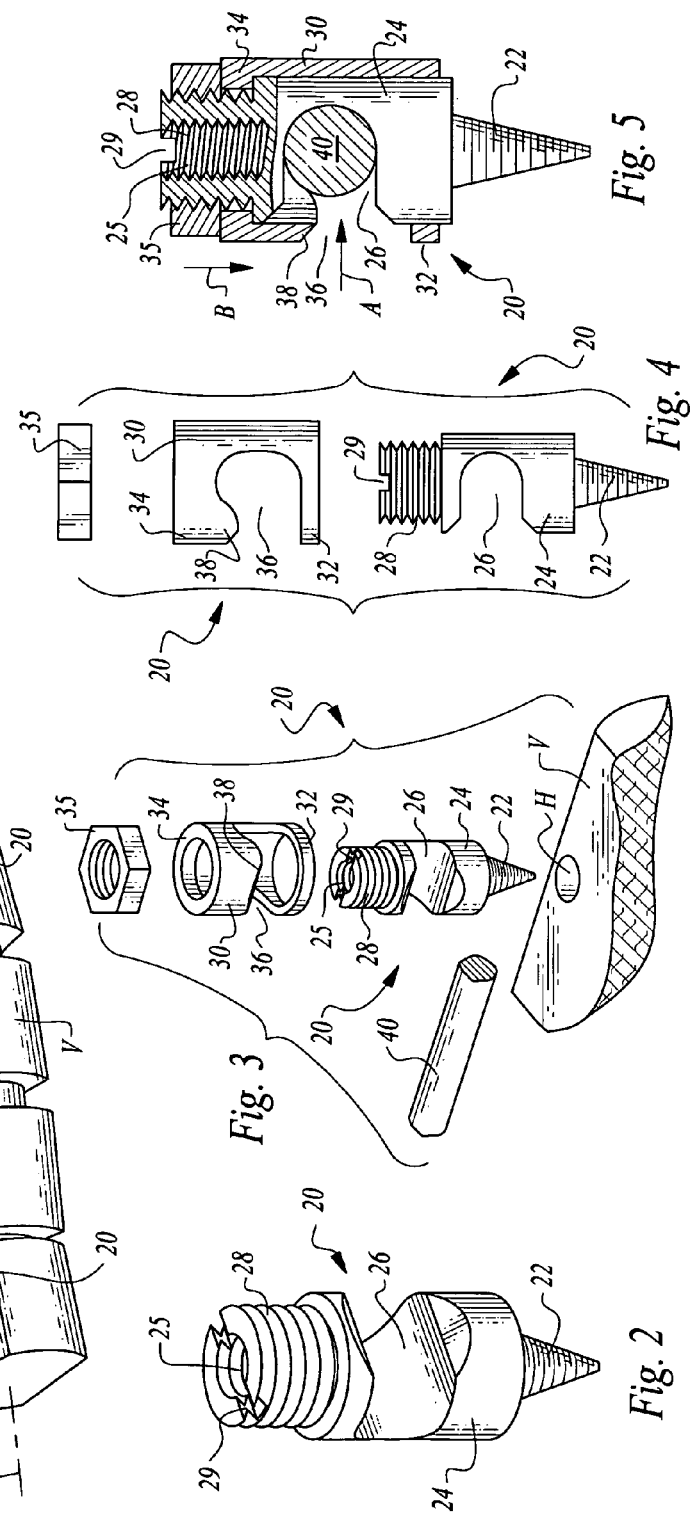

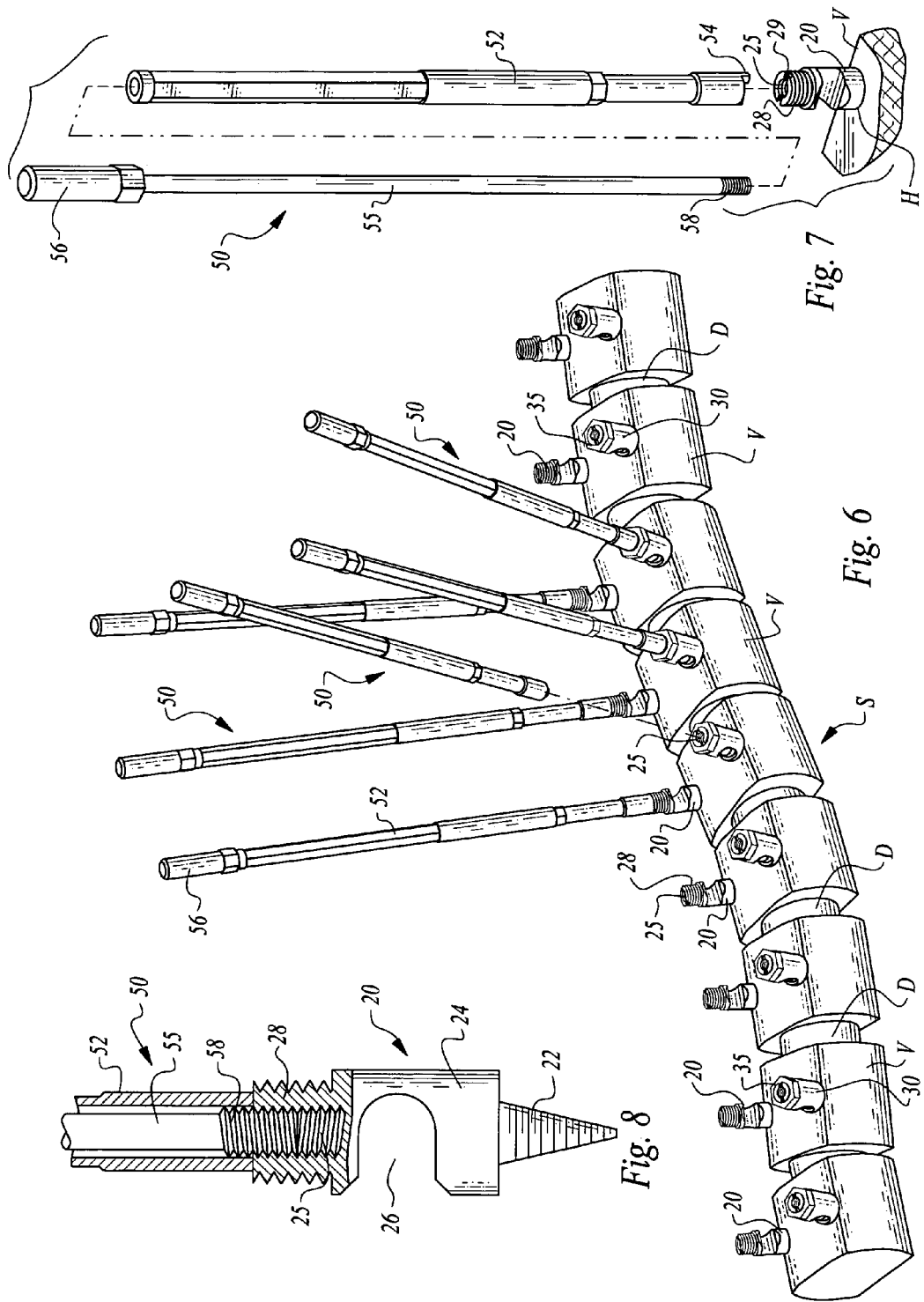

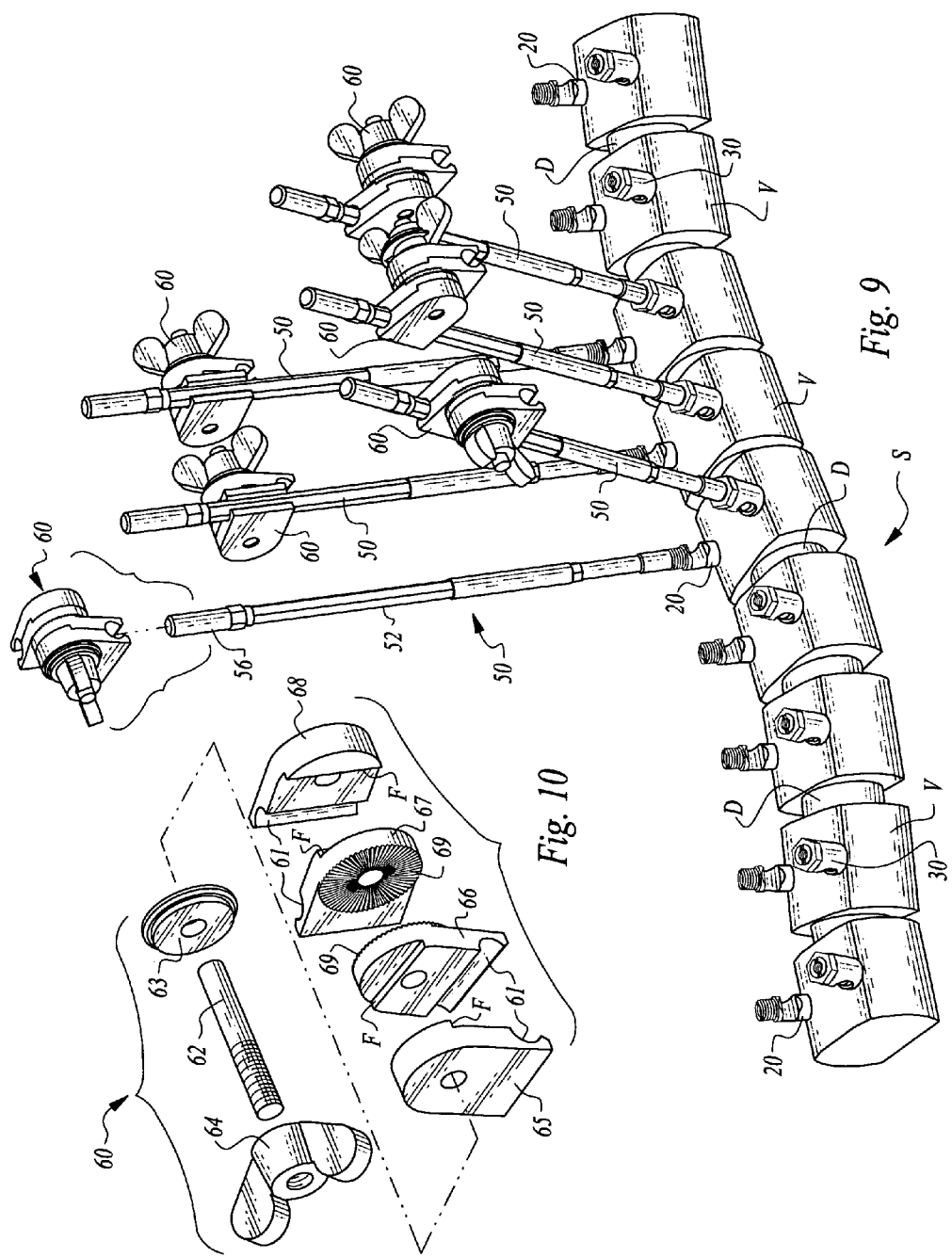

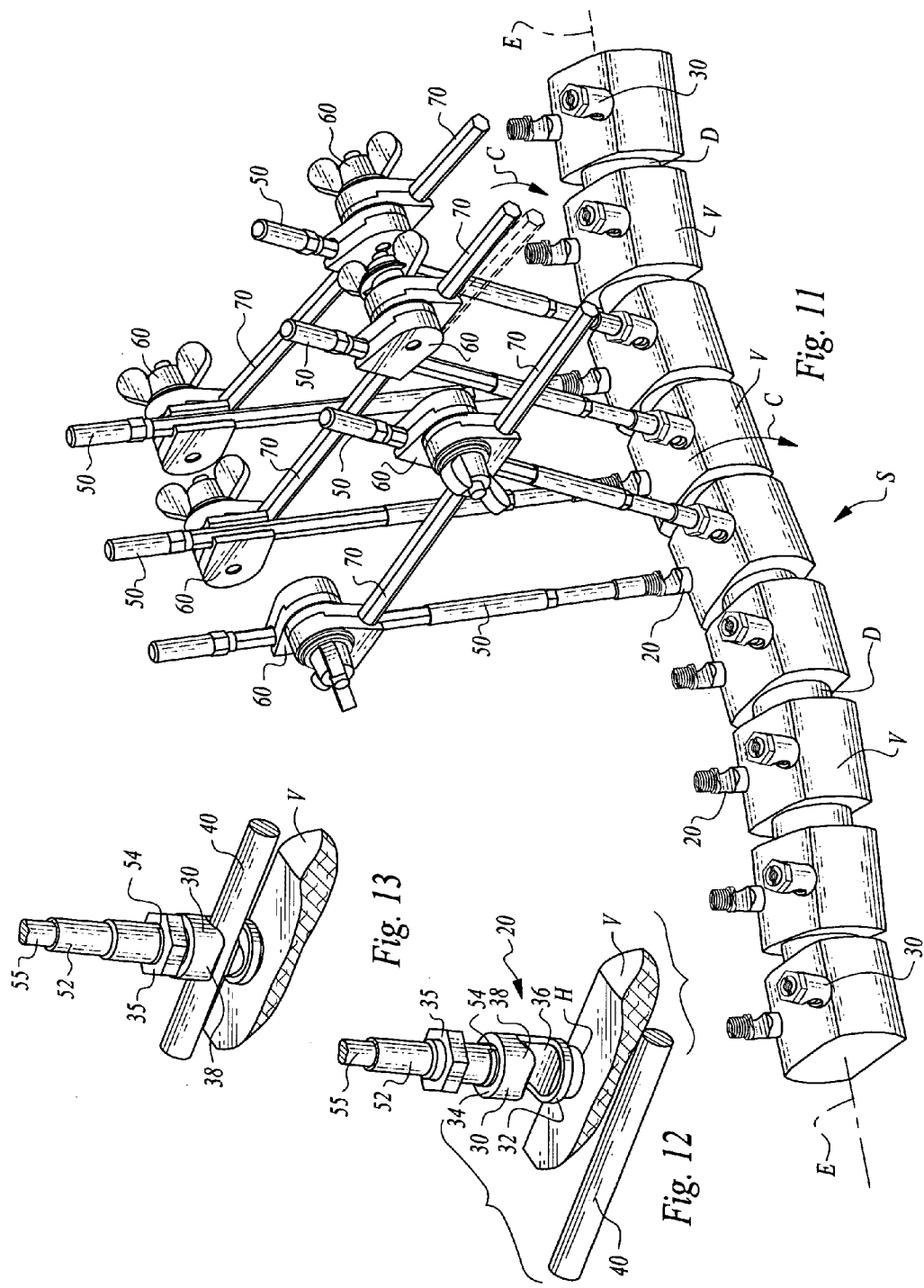

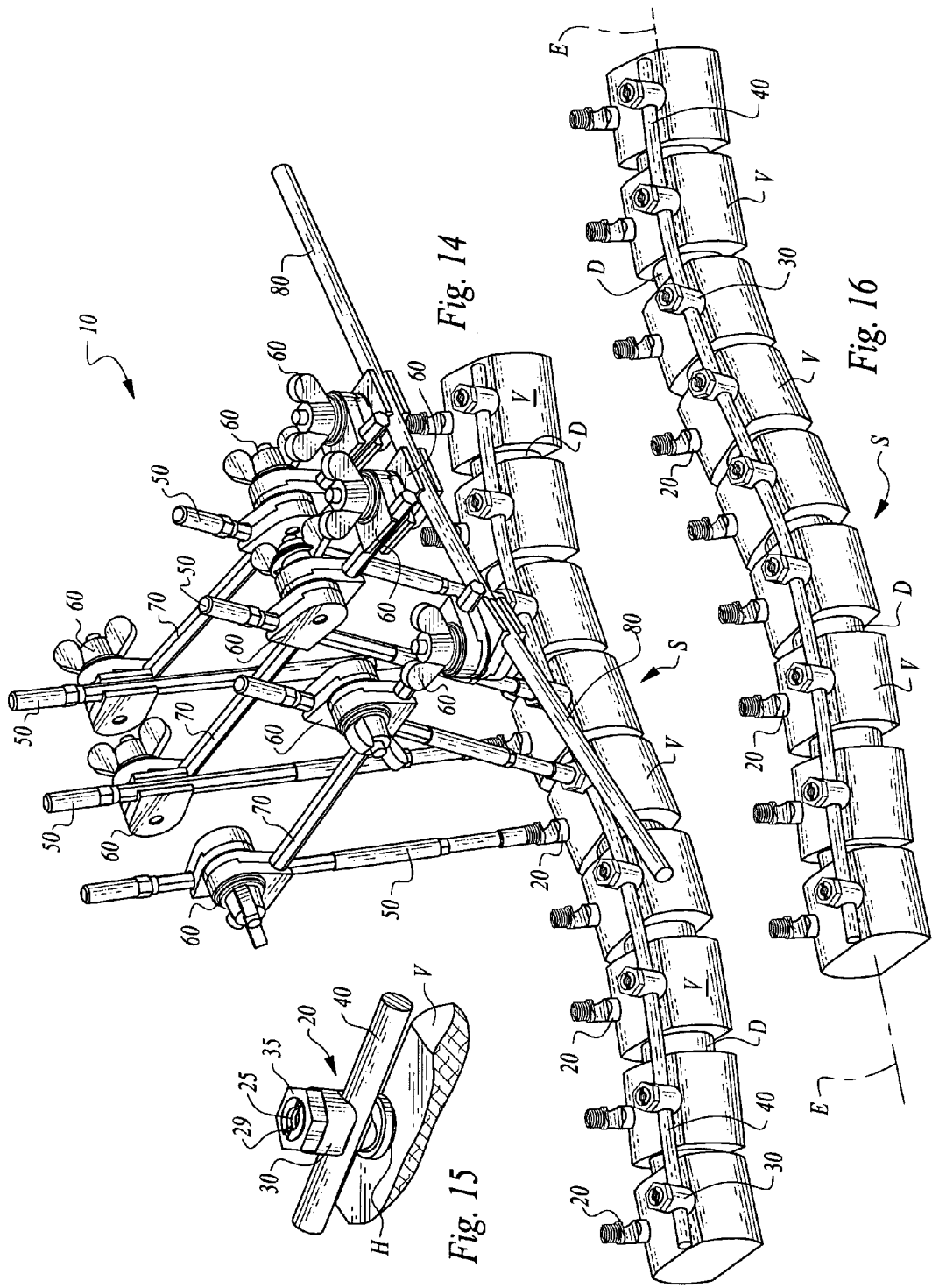

SCOLIOSIS DE-ROTATION SYSTEM AND METHOD

FIELD OF THE INVENTION

The following invention relates to methods and apparatuses for use in surgical procedures to treat structural deficiencies in the spine. More specifically, this invention relates to surgical methods and apparatuses for adjusting improper rotation of vertebra relative to a central axis of the spine, such as in cases of scoliosis where individual vertebra are undesirably mis-rotated out of a proper alignment.

BACKGROUND OF THE INVENTION

A primary characteristic of scoliosis is that an elongate central axis of the spine is curved rather than straight, when viewed posteriorly or anteriorly. Such cases of scoliosis can vary between minor and severe. In more severe cases, one treatment is to intervene surgically, aligning the individual vertebra of the spine together to reform the elongate central axis of the spine to be linear (when viewed posteriorly or anteriorly), and then to fuse certain of the disk spaces between adjacent vertebrae to hold the vertebrae in this new position.

To assist in holding the vertebrae in the desired position during fusion of adjacent vertebrae together, it is known to place pedicle screws into the pedicles of the vertebrae and to attach heads of the pedicle screws to one or more elongate spine rods. Such fusion with pedicle screws and spine rods is also known to treat other conditions other than scoliosis, such as where injury has occurred to the spine or disks within the spine have degenerated and fusion is indicated. The pedicle screws and spine rods generally remain implanted even after the adjacent vertebra have fused together and are formed of biocompatible materials to minimize any adverse consequences associated with such permanent implantation.

One such system that provides the hardware components for such procedures is the "Universal Spine System" ("USS") provided by Synthes, Inc. whose United States headquarters is in West Chester, Pa. The USS includes pedicle screws and spine rods as well as extension posts for pedicle screws and other associated hardware.

Certain cases of scoliosis, as well as potentially other conditions, are characterized in that at least one vertebra is rotated about the central axis of the spine out of alignment relative to a desired orientation for the vertebra. Such a vertebra can be either in a proper position but only in an undesirable rotation or can be both in an improper position and rotated to an improper orientation. Prior art spinal fusion hardware and procedures, including those in Synthes' USS, have not adequately dealt with such vertebral mis-rotation. Thus leaving the patient to suffer from the consequences of such mis-rotation.

Furthermore, when a vertebra is mis-rotated into an improper position, a surgeon is to some extent thwarted in properly placing pedicle screws and properly attaching heads of the pedicle screws to an adjacent elongate spine rod. For instance, where a vertebra is mis-rotated and a pedicle screw is attached to the pedicle of the vertebra in the typical fashion, the head of the pedicle screw is not where it needs to be to attach to the elongate and substantially linear spine rod.

Ligaments and other bodily structures tend to hold a mis-rotated vertebra in its mis-rotated position, making it difficult for the surgeon to manually de-rotate the vertebra to is proper position and hold it in this de-rotated position while anchoring it to the spine rod. Accordingly, a need exists for a method and apparatus for de-rotating a mis-rotated vertebra and to hold the mis-rotated vertebra in the proper de-rotated position, so that an elongate spine rod can be affixed to the pedicle screws, thus holding the mis-rotated vertebra can be held in its proper and de-rotated position while adjacent vertebra fuse together.

While this problem of mis-rotation of vertebra is described in the context of scoliosis and other spine conditions where fusion of adjacent vertebra together is indicated, de-rotation of mis-rotated vertebra could conceivably also beneficially be provided complimentary to procedures on the spine other than spinal fusion, such as disk replacement procedures or disk therapy procedures or other spinal procedures that do not involve vertebral fusion.

SUMMARY OF THE INVENTION

Accordingly, with this invention a system and method are provided for de-rotation of a mis-rotated vertebra, such as during a spinal fusion procedure to correct severe cases of scoliosis which include vertebral mis-rotation. As with many other spinal fusion procedures, pedicle screws are attached to pedicles of vertebra to be de-rotated, as well as vertebra adjacent the vertebra to be de-rotated. Preferably, each of the two pedicles of each vertebra involved has a pedicle screw attached thereto, while potentially in some instances a single pedicle screw within a single pedicle of the vertebra involved could be provided with a pedicle screw.

The pedicle screws are preferably of a known type such as provided as part of the Synthes, Inc. USS, which leaves an uppermost portion of each head of each pedicle screw accessible for attachment of a post thereto, while also being simultaneously accessible for attachment of an elongate spine rod between adjacent pedicle screws of adjacent vertebrae. Such posts are also known in systems such as the Synthes, Inc. USS. In one preferred form of the invention, the head of each pedicle screw includes a side slot which can receive the elongate spine rod therein. An uppermost portion of the head is provided with a threaded bore to which a lower end of a post can attach to the pedicle screw. Other forms of attachment other than the threaded bore could alternatively be provided, such as a form of removably attachable joint which can secure the lower end of the post to the upper end of the pedicle screw.

The pedicle screws are configured so that they can removably grasp the elongate spinal rod with the posts also attached to the heads of the pedicle screws. For instance, a cap can be provided over the head of each pedicle screw along with a nut. This cap can be provided with a cleft in a side thereof which can be aligned with a side slot in the head of the pedicle screw to allow the spine rod to pass into the side slot of the pedicle screw, and then the cap can be tightened, such as by engaging the nut with a threaded crown on the head above the side slot, in a manner closing the side slot in the head of the pedicle screw sufficiently to keep the spine rod captured within the head of the pedicle screw. Such pedicle screws are a generally known individual hardware component of many pedicle screws, such as some in the Synthes, Inc. USS.

The posts extend up from the pedicle screw, preferably substantially axially aligned with a long axis of each pedicle screw. The posts thus provide leverage against which a surgeon or other user can apply forces, in a rotational manner about the spine central axis, to cause the vertebra associated with the post to be de-rotated as desired.

A holder is provided which can hold the posts after they have been positioned for de-rotation of the spine to an extent desired. This holder is most preferably in the form of an elongate de-rotation rod which can couple together posts associated with separate vertebrae. In a most preferred form of the invention, a pair of posts associated with each vertebra are joined together by a bar. One bar is associated with each vertebra and the posts and/or bars can be manipulated by the surgeon to de-rotate the spine as desired. Once the de-rotation has occurred, the individual bars can be fixed to the elongate de-rotation rod to hold the bars, as well as the associated posts and the associated vertebra in the desired position after the de-rotation has been completed.

The de-rotation rods hold these vertebra in the de-rotated position while the surgeon is then freed up to place the spine rod in to the side slots in the heads of the pedicle screws and secure the spine rod to the pedicle screws. Once so secured, the de-rotation of the vertebra is fixed and prevented from returning to a mis-rotated improper alignment. This de-rotation procedure can precede or follow a spinal fusion procedure that would typically involve removing disks from associated intervertebral spaces and use of other techniques and implantable medical devices known in the art to complete the spinal fusion procedure.

In one embodiment the spinal fusion procedure is conducted posteriorly or posterior-laterally such that the entire procedure including the de-rotation as well as the spinal fusion can occur without requiring anterior access to the spine. As an alternative, two separate parts of the procedure can involve the de-rotation and installation of the spinal rods and associated pedicle screws in a posterior procedure preceded or followed by an anterior procedure where the spinal fusion or other disk space therapy procedure is completed. At the end of the procedure, the posts and any associated bars and the de-rotation rod are removed, with the pedicle screws and spine rods typically remaining at the implantation site.

OBJECTS OF THE INVENTION

Accordingly, a primary object of the present invention is to provide a method for de-rotating a mis-rotated vertebra, such as while treating certain cases of scoliosis through a spinal fusion procedure.

Another object of the present invention is to provide a system for de-rotating a mis-rotated vertebra.

Another object of the present invention is to provide a vertebra de-rotation procedure which can be performed posteriorly and in a minimally invasive manner.

Another object of the present invention is to provide a tool for de-rotating a vertebra and holding the vertebra in a proper and de-rotated position while other procedures, such as attachment of a spine rod to pedicle screws, can be completed.

Another object of the present invention is to provide a de-rotation system for a vertebra which can maintain access to heads of the pedicle screws for attachment of a spine rod thereto at various different stages in a surgical procedure.

Another object of the present invention is to provide a tool for de-rotating a vertebra and holding the vertebra in a de-rotated position.

Another object of the present invention is to provide a method for treating scoliosis cases that also include vertebral mis-rotation.

Other further objects of the present invention will become apparent from a careful reading of the included drawing figures, the claims and detailed description of the invention.

BRIEF DESCRIPTION OF THE DRAWINGS

FIG. 1 is a perspective view of a simplified depiction of a spine with multiple vertebra generally represented by simplified geometric blocks, and indicating an initial step in a method according to this invention where pedicle screws are attached to at least some of the vertebrae within the spine.

FIG. 2 is a perspective view of a head of one of the pedicle screws shown in FIG. 1 and showing various different structural details of the pedicle screw according to a preferred embodiment of this invention.

FIG. 3 is an exploded parts perspective view of the pedicle screw as well as a spine rod and cap and nut for securing the spine rod to the pedicle screw according to a preferred embodiment of this invention.

FIG. 4 is a side elevation exploded parts view of that which is shown in FIG. 3.

FIG. 5 is a full sectional view of the pedicle screw and associated cap and nut, and with the spine rod captured therein.

FIG. 6 is a perspective view of the spine of FIG. 1, after posts have been attached to some of the pedicle screws and extending up from the pedicle screws.

FIG. 7 is a perspective view of a single post and a single pedicle screw and with the shaft and sleeve of the post shown exploded away from each other and illustrating how the post is attached to the pedicle screw.

FIG. 8 is a sectional side elevation view of an interface between the head of the pedicle screw and the lower end of the post, illustrating further how the post is removably attached to the head of the pedicle screw.

FIG. 9 is a perspective view similar to that which is shown in FIGS. 1 and 6, but after clamps have been further attached to the posts for attachment of the posts either directly to a de-rotation rod or to the de-rotation rod through intervening bars.

FIG. 10 is a perspective exploded parts view of a single clamp illustrating one configuration for a fastener according to a preferred embodiment.

FIG. 11 is a perspective view similar to that which is shown in FIGS. 1, 6 and 9, illustrating a further step where bars have been attached to clamps to join posts of a common vertebra together. A bar shown in broken lines illustrates how a bar associated with a mis-rotated vertebra can be moved along with associated posts to cause the mis-rotated vertebra to be de-rotated into proper position.

FIG. 12 is a perspective view of an interface between the head of the pedicle screw and the lower end of a post and illustrating a first step in capturing a spine rod therein, when a post is simultaneously attached to the pedicle screw.

FIG. 13 is a perspective view similar to that which is shown in FIG. 12, but after the spine rod has been captured by the pedicle screw head.

FIG. 14 is a perspective view similar to FIGS. 1, 6, 9 and 11, but further showing the use of clamps to secure the bars associated with separate vertebra to a common de-rotation rod to hold a mis-rotated vertebra in a proper de-rotated position, and further showing the placement of a spine rod into side slots in the heads of the pedicle screws to hold the vertebra in the proper and de-rotated position.

FIG. 15 is a perspective view of a head of a single pedicle screw holding the spine rod therein and after removal of the post associated with the pedicle screw.

FIG. 16 is a perspective view similar to that which is shown in FIGS. 1, 6, 9, 11 and 14, but after removal of all of the posts and associated bars and de-rotation rod, and illustrating how the spine rod remains attached to the pedicle screws and how the vertebra remains de-rotated. While only a single spine rod is shown in FIG. 16, typically two spine rods would be attached to opposite ones of the pairs of pedicle screws with the two rods being generally parallel with each other.

DESCRIPTION OF THE PREFERRED EMBODIMENT

Referring to the drawings, wherein like reference numerals represent like parts throughout the various drawing figures, reference numeral 10 (FIG. 14) is directed to a system for de-rotation of a vertebra V within a spine S, where the vertebra V has been mis-rotated, such as exhibited along with a scoliosis condition. The system 10 operates upon a spine S including multiple vertebrae V spaced apart by disks D. The system 10 is useful according to a method depicted in steps from FIGS. 1, 6, 9, 11, 14 and 16 in sequence to de-rotate a vertebra V that has been mis-rotated about the elongate central axis E of the spine S. The de-rotation method can be accomplished as part of an overall spinal fusion procedure where a spine rod 40 secures the vertebrae V in a desired position through pedicle screws 20, or this de-rotation method can accompany some other spinal procedure.

In essence, and with particular reference to FIG. 14, the basic details of the various parts of the system 10 are described, according to a most preferred embodiment. The system 10 includes multiple pedicle screws 20, preferably with two pedicle screws 20 attached to each vertebra V. A cap 30 is associated with each pedicle screw 20 for securing a spine rod 40 to the pedicle screws 20. Posts 50 extend up at least some of the pedicle screws 20, preferably coaxial with a centerline of each pedicle screw 20. The posts 50 are removably attachable to the pedicle screws 20 in a manner which allows the spine rod 40 to be attached to the pedicle screws 20 while they are simultaneously also attached to the posts 50.

Clamps 60 are provided as part of a preferred form of fastener within a holder for holding the posts relative to each other. Most preferably, this holder also includes bars 70 which connect through clamps 60 to hold pairs of posts 50 associated with common vertebra together. Further clamps 60 act as a preferred form of second fasteners to allow the bars 70 to be coupled to at least one de-rotation rod 80 so that vertebra that have been de-rotated by rotation of bars 70 and associated posts 50 can be held to the de-rotation rods 80 to hold such vertebra in a de-rotated and proper position. Once the vertebra has been de-rotated, the spine rod 40 can be coupled to each pedicle screw 20 to hold the vertebra V where desired. The posts 50, bars 70 and de-rotation rods 80 are then removed at the end of the de-rotation procedure.

More specifically, and with particular reference to FIGS. 1-5, particular details of the pedicle screw 20 and associated caps 30 for securing the spine rod 40 to the pedicle screw 20, are described according to a most preferred embodiment. The pedicle screws 20 provide a preferred form of means to attach the lower end of each post 50 to a vertebra V. The post 50 could alternatively attach to the vertebra through other attachment mechanisms such as facet screws or brackets attached to portions of the vertebra other than the pedicle, or by direct attachment to the vertebrae, such as by threading a lower end of each post directly into a pedicle of a vertebra V.

The pedicle screws 20 in this preferred embodiment include an elongate threaded shaft 22 adapted to be anchored within a pedicle of the vertebra V, and a head 24 on an end thereof opposite the threaded shaft 22. The threaded shaft 22 can have any form known for pedicle screws in the prior art, and fits within a hole H (FIG. 3) in the vertebra V which can be pre-drilled and tapped, or pre-drilled with the threaded shaft 22 being self-tapping, or formed by the shaft 22 without pre-drilling. While two pedicle screws 20 are preferably attached to each vertebra V, conceivably only one pedicle screw 20 could be attached to at least some vertebra V and still provide at least some of the benefits according to this invention.

The head 24 includes a side slot 26 sized to allow an elongate spine rod 40 to fit into the side slot 26 for attachment to the head 24. An end of the head 24 opposite the threaded shaft 22 includes a threaded crown 28 thereon with external threads sized to be complemental with a nut 35 described below.

The threaded crown 28 includes a threaded bore 25 extending along a central axis down into the threaded crown 28. This threaded bore 25 has female threads configured to mesh with a threaded tip 58 on a lower end of the posts 50. The threaded bore 25 within the threaded crown 28 thus provides a preferred form of means to securely and removably join the lower end of each post 50 to the head 24 of each pedicle screw 20. A slot 29 is formed at an uppermost end of the head 24. This slot 29 not only allows for a torque applying tool to interface with pedicle screw 20, but also can interface with a tab 54 at a lower end of a sleeve 52 portion of the post 50, such that rotational forces can be applied from the post 50 down to the pedicle screw 20. This slot 29 and tab 54 can also interface to prevent unwanted rotation between the posts 50 and the pedicle screws 20.

A cap 30 is preferably provided overlying each head 24 to hold the spine rod 40 within the side slot 26 in the head 24 of each pedicle screw 20. Each cap 30 is preferably a rigid generally cylindrical structure which includes a lower collar 32 opposite an upper collar 34. The lower collar 32 is sized to reside over the head 24 of the pedicle screw 20. The upper collar 34 has an interior diameter too large to fit entirely over the head 24 but sufficiently large to allow the threaded crown 28 to extend up through the upper collar 34. Also, when the cap 30 is pressed down, the upper collar 34 abuts portions of the head 24 below the threaded crown 28.

A cleft 36 is formed in a side of the cap 30. This cleft 36 is between the lower collar 32 and upper collar 34 and extends only partially laterally into a hollow interior of the cap 30. The cleft 36 is somewhat similar in size and shape to the side slot 26 of the pedicle screw 20. In particular, the cleft 36 is large enough to allow the spine rod 40 to pass laterally thereinto. Uniquely, the cleft 36 includes a lip 38 on an upper portion thereof. This lip 38 extends down slightly thus blocking the spine rod 40 from removal out of the side slot 26 when the cap 30 is tightly fastened over the head 24 of the pedicle screw 20.

When the cap 30 is loosened and can move up slightly relative to the head 24, the spine rod 40 can pass through both the cleft 36 and side slot 26. Such insertion of the rod 40 into the side slot 26 occurs along arrow A of FIG. 4. A nut 35 is provided adjacent the upper collar 34 of the cap 30. This nut 35 has female threads which interface with male threads on the threaded crown 28. As the nut 35 is tightened, the cap 30 is secured down over the head 24 and the lip 38 of the cleft 36 closes off the side slot 26 sufficiently (along arrow B of FIG. 5) to keep the spine rod 40 from being able to come out of the side slot 26.

The posts 50 are preferably of sufficiently small diameter that the nut 35 and cap 30 can ride up over at least lower portions of the posts 50, such that the cap 30 can be moved up and down relative to the head 24 of the pedicle screw 20 when the cap 30 is not tightened by the nut 35, to facilitate rod 40 insertion into the side slot 26. Such positioning of the nut 35 and cap 30 relative to the head 24 of the pedicle screw 20 is further depicted in FIGS. 12 and 13. In FIG. 12 the head 24 portion of the pedicle screw 20 is removed to most clearly show details of the cap 30. When the nut 35 is tightened down against the cap 30 (as shown in FIGS. 5 and 13) the lip 38 closes off the side slot 26 sufficiently so that the rod 40 is captured within the head 24 of the pedicle screw 20.

With particular reference to FIGS. 6-8, particular details of the posts 50 and their interconnection with the pedicle screws 20 are described, according to a most preferred embodiment. Each post 50 preferably includes a two part structure including an elongate linear sleeve 52 having a hollow bore passing entirely therethrough and a shaft 55 which resides within the sleeve 52. A lower end of the sleeve 52 preferably includes a tab 54 therein which can reside within the slot 29 at the uppermost end of the threaded crown 28 of the head 24 of the pedicle screw 20.

The shaft 55 is preferably longer than the sleeve 52 and includes a threaded tip 58 at a lower end of the shaft 55 and a grip 56 at an upper end of the shaft 55. Because the shaft 55 is longer than the sleeve 52, the threaded tip 58 can extend out of a lower end of the sleeve 52 to threadably engage the threaded bore 25 and the head 24 of the pedicle screw 20 while the grip 56 extends out of an upper end of the shaft 55, to be gripped by a hand of a user or by a torque applying tool.

The grip 56 can include a faceted structure to facilitate engagement with a torque applying tool. Similarly, portions of the sleeve 52 can include a faceted band for engagement with a torque applying structure. When the slot 29 and tab 54 have engaged each other, the faceted band on the shaft 55 can be used to allow a torque applying tool to rotate the pedicle screw 20 if required, such as to align the side slots 26 of multiple pedicle screws 20 to face in a common direction. Tightening of the posts 50 can occur by rotation of the grip 56, either by hand or through utilization of the faceted region on the grip 56, to tighten the threaded tip 58 down into the threaded bore 25 of the pedicle screw 20. Details of this engagement through the sleeve 52 and shaft 55 of the posts 50 with the head 24 of the pedicle screw 20 is particularly shown in FIG. 8 in full section.

While the posts 50 are shown in this preferred two part structure, it is conceivable that the posts 50 could be a unitary elongate mass in a simplified form of this invention which merely has a threaded tip which threads into the threaded bore 25 of the pedicle screw 20, or otherwise engages with the vertebra.

The posts 50 provide a lever arm to more easily apply de-rotation forces (about arrow C of FIGS. 1 and 11) to properly orient a mis-rotated vertebra V. The longer that the posts 50 are, the less force is required to de-rotate the vertebra V. Posts 50 attach to adjacent vertebrae which do not require de-rotation and are thus provided as reference points so that de-rotation of a mis-rotated vertebra V does not cause adjacent vertebra V to also be rotated. Most preferably, two posts 50 are attached to each vertebra V. Thus, a user can grip either one of the posts 50 to apply the desired de-rotation forces. When the bars 50 join the posts 50 of each vertebra V together, de-rotation forces can be applied to either post 50 or to the bar 70 and each of the posts 50 and bar 70 rotate together, such that de-rotation forces applied to the vertebra V are distributed over the two pedicle screws 20, rather than being concentrated at a single point on the mis-rotated vertebra V.

With particular reference to FIGS. 9 and 10, details of the clamps 60 for joining the posts 50 either directly to a de-rotation rod 80, or to the de-rotation rod 80 through bars 70, are described. These clamps 60 provide one form of fastener which can couple portions of the posts 50 spaced from the lower ends of the posts 50 to adjacent structures such as the bars 70 or de-rotation rods 80. These clamps 60 also provide a portion of a holder in a preferred form of this invention. The basic function of the holder is to hold the posts 50 associated with separate vertebra V in a desired position with the mis-rotated vertebra de-rotated, which holder can involve direct coupling of the posts 50 together or indirect coupling of the posts 50 through intervening structures such as multiple clamps 60, as well as the de-rotation rods 80.

While the clamps could have a variety of different configurations, the clamps 60 preferably include multiple separate parts including an elongate axle 62 with a wing nut 64 threadably attached thereto. A washer 63 resides along the axle 62 and is located adjacent the wing nut 64. Four plates including a bar outer plate 65, bar inner plate 66, post inner plate 67 and post outer plate 68 are preferably sequentially provided upon the axle 62, with each of these plates including a central hole which floats on the axle 62. Most preferably, the last plate in the form of the post outer plate 68 is affixed to the axle 62 with the other plates 65, 66, 67 sandwiched between the wing nut 64 and washer 63 on one end and the post outer plate 68 on the other end.

Each plate 65, 66, 67, 68 preferably includes one cylindrical trough 61 which is shaped to conform to a portion of a post 50 or bar 70 or rod 80. When adjacent plates 65, 66 or plates 67, 68 are clamped together by action of the wing nut 64, the cylindrical troughs 61 are aligned with a post 50, bar 70 or de-rotation rod 80 therein, to securely hold the clamp 60 to such a post 50, bar 70 or rod 80. With one structure such as a post 50, bar 70 or rod 80 in one of the pairs of troughs 61 between adjacent plates 65, 66 or plates 67, 68, and the other pair of plates 67, 68 or plates 65, 66 capturing a structure such as another post 50, bar 70 or rod 80, the two separate rigid structures are effectively clamped together.

Axial orientation between these two structures including a post 50, bar 70 and rod 80 can be selected and held by providing radial notches 69 between the bar inner plate 66 and post inner plate 67. Preferably facets F are provided between the pairs of plates 65, 66 and the pairs of plates 67, 68 to further discourage relative rotation between the pairs of plates 65, 66 and the pairs of plates 67, 68.

When the wing nut 64 is positioned so that the clamps 60 are somewhat loose, the clamps 60 can have associated elongate structures positioned within the cylindrical troughs 61. The angular orientation of the two elongate structures can the be selected and the wing nut 64 tightened to secure the entire clamp 60 assembly to secure the two elongate items taken from the group including a post 50, a bar 70 and a de-rotation rod 80, to secure the two elongate structures together.

Other forms of fasteners, other than the clamps 60 could alternatively be utilized which are either of a permanent or an adjustable variety, with adjustability most preferred. Alternatives to the wing nuts 64 could include faceted structures to which a torque applying tool can engage, or a thumb wheel which can allow a user to apply a relatively high amount of force while still being generally low profile. Most preferably, two clamps 60 are provided on each bar 70 which join each bar 70 to two posts 50 coupled to pedicle screws 20 on a common vertebra V. An additional clamp 60 is preferably utilized at an end of each bar 70 to join that bar 70 to a de-rotation rod 80. Conceivably, two de-rotation rods 80 could be provided so that a clamp 60 would be provided at each end of the bar 70 to join each end of the bar 70 to a separate de-rotation rod 80 (FIG. 14). The bars 70 are shown as having a hexagonal structure but could alternatively be cylindrical or have other generally constant cross-sectional elongate forms.

The de-rotation rods 80 are preferably similar to the elongate spine rod 40 and are preferably substantially rigid elongate structures. Most preferably, the de-rotation rods 80 are entirely linear or only curved slightly and in an amount of curvature generally matching a desired amount of curvature in the spine S. For instance, a lordosis angle in the spine S can be facilitated to some extent by having the de-rotation rods 80 match this degree of curvature, but with the rods 80 straight when viewed posteriorly or anteriorly.

With particular reference to FIGS. 1, 6, 9, 11, 14 and 16, the method utilizing the system 10 of this invention is described, according to a preferred embodiment for de-rotating a mis-rotated vertebra V. In a first step (FIG. 1) vertebra that are mis-rotated have at least one pedicle screw 20 attached thereto, and preferably a pair of pedicle screws 20. Furthermore, vertebrae V adjacent the mis-rotated vertebra V are also fitted with pedicle screws 20 anchored thereto. Preferably, vertebrae V on both sides of the mis-rotated vertebra V are fitted with pedicle screws to act as reference vertebrae for de-rotation of the mis-rotated vertebra V (arrow C depicts a desired direction of de-rotation of a vertebra V in an exemplary embodiment).

With particular reference to FIG. 6, a second step in the process is illustrated where posts 50 are attached to each of the pedicle screws 20. These posts 50 extend axially up from each of the pedicle screws 20. The posts 50 are preferably secured to the pedicle screws 20 so that they are immobile relative to each pedicle screw 20. A user can then access ends of the posts 50 opposite the pedicle screws 20 to apply de-rotation forces as desired to de-rotate the vertebra V within the spine S.

While such de-rotation can be effectively provided merely with utilization of the posts 50 and being manipulated by hands of the user, it is desirable that de-rotation be maintained by holding the posts 50 in the required position after such de-rotation. Otherwise, ligaments and other body structures have a tendency to return the mis-rotation back to the de-rotated vertebra V. Such a holder is preferably provided in the form of the bars 70 joined to the posts 50 by clamps 60, as well as the de-rotation rod 80. One bar 70 is provided for each pair of posts 50 associated with a common pair of pedicle screws 20 on a common vertebra. The bar 70 is provided approximately perpendicular to the posts 50 and attached to each of the posts 50 with clamps 60. The bars 70 preferably extend past one of the posts 50 a sufficient distance to allow another clamp 60 to secure the bar 70 to a de-rotation rod 80.

Such placement of the bars 70 with the clamp 60 is depicted in FIG. 11. Further attachment of the de-rotation rod 80 to ends of the bars 70 through clamps 60 is depicted in FIG. 14. Preferably, at a minimum a vertebra V to be de-rotated is positioned between two vertebrae V which are not mis-rotated. The mis-rotated vertebra V is de-rotated by rotation of the entire assembly including the pair of posts 50 and the associated bar 70 attached to the mis-rotated vertebra (by rotation along arrow C of FIG. 11).

Once this de-rotation has occurred, the de-rotation rods 80 can be fastened with clamps 60 to each of the bars 70. Such clamping holds the de-rotated vertebra V in its desired de-rotated position. At this stage, not only has a mis-rotated vertebra V been de-rotated, but it is being securely held in the de-rotated position. A user can then utilize a spine rod 40 to fix the vertebra V relative to each other. In particular, the spine rod 40 is translated laterally into the side slot 26 in the head 24 of each pedicle screw 20 (along arrow A of FIG. 5). The various caps 30 of each pedicle screw 20 are then tightened down through rotation of the nuts 35 to allow the caps 30 to capture (by motion along arrow B of FIG. 5) the spine rod 40 within each head 24 of each pedicle screw 20. Once the caps 30 have been tightened down onto the heads 24 of the pedicle screws 20, the spine rod 40 (or pair of spine rods 40) secures the vertebra V together and preserves the de-rotation of the vertebra V. The posts 50 and associated bars 70 and de-rotation rods 80 can then be removed leaving only the pedicle screw 20 and spine rod 40. While a single spine rod 40 is shown in FIG. 16, a pair of spine rods 60 would typically be utilized.

The overall de-rotation procedure can be followed by a spinal fusion procedure to fuse adjacent vertebra V together, such as by removal of disks D between the vertebra V and utilization of known techniques in implantable medical devices to accomplish such spinal fusion. Such spinal fusion can occur posteriorly, posterior-laterally or anteriorly after the completion of the attachment of the spine rods 40 and completion of the overall de-rotation procedure. As another alternative, the spinal fusion procedure can begin and then the de-rotation procedure can follow at least partially afterwards. The de-rotation system and method of this invention can also conceivably be utilized as a portion of a procedure other than a spinal fusion procedure where de-rotation of a vertebra V is indicated.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A system for de-rotation of a vertebra within a spine, the system comprising in combination:
    a plurality of pedicle screws, each said pedicle screw including a threaded shaft adapted to be anchored within a pedicle of a vertebra and with a head on an end of said threaded shaft;
    at least one elongate spine rod orientable substantially parallel with an elongate central axis of the spine;
    each said head of each said pedicle screw configured so that it can be secured to said rod;
    a plurality of substantially rigid elongate posts, each said post having a lower end opposite an upper end, said lower ends each adapted to be removably affixed to one of said heads of one of said pedicle screws;
    a post holder coupled to at least two of said plurality of posts on portions of said posts spaced from said lower ends of said posts and holding said posts relative to each other;
    wherein each said pedicle screw is adapted to be secured to said spine rod and released from said spine rod when said posts are simultaneously affixed to said pedicle screw;
    wherein said head of said pedicle screw includes a side slot therein, said side slot sized at least as large as a diameter of said elongate spine rod, said side slot extending into said head in a direction lateral to a long axis of said threaded shaft of said pedicle screw, said pedicle screw further including a cap adapted to move up and down relative to said head, said cap adapted to selectively close said side slot and said head to selectively hold and release said elongate spine rod within said side slot of said head of said pedicle screw;

wherein said cap includes a cleft in a side thereof, said cleft sized sufficiently large to allow said elongate spine rod to pass therethrough, said cleft having a contour distinct from that of said side slot, such that when said cap is secured to said head, said rod is held within said side slot;

wherein said head of said pedicle screw includes a threaded bore extending along a long axis of said pedicle screw, said post adapted to engage said threaded bore to secure said post to said pedicle screw; and wherein said post includes a shaft with a threaded tip adapted to thread into said threaded bore in said head of said pedicle screw, said post also including a sleeve with said shaft residing within said sleeve, said shaft being longer than said sleeve such that said threaded tip extends beyond a first end of said sleeve and a grip on an end of said shaft opposite said threaded tip extends beyond a second end of said sleeve opposite said first end of said sleeve.

2. The system of claim 1 wherein said pedicle screw includes a threaded crown on an end of said head opposite said threaded shaft, said threaded crown including said threaded bore therein, a nut adapted to be threadably attached to outer threads on said threaded crown, said cap adapted to reside over said head with an upper collar adjacent a transition between said threaded crown and other portions of said head of said pedicle screw, said nut adapted to hold said cap down upon portions of said head of said pedicle screw below said threaded crown when said nut engages threads of said threaded crown, such that tightening of said nut tightens said cap relative to said head of said pedicle screw, said nut open to preserve access to said threaded bore in said head through said nut, said nut and said cap sized to slide up over said threaded tip and said sleeve of said post at least partially, such that said side slot of said head of said post can be opened and closed for removably securing said elongate spine rod within said side slot when said post is coupled to said head of said pedicle screw through said threaded bore in said head of said pedicle screw.

* * * * *